United States Patent
Williams et al.

(10) Patent No.: US 10,053,426 B2
(45) Date of Patent: Aug. 21, 2018

(54) PROCESS FOR THE SYNTHESIS OF METYRAPONE AND ALKYLATED METYRAPONE ANALOGS

(71) Applicant: Albemarle Corporation, Baton Rouge, LA (US)

(72) Inventors: Eric L. Williams, Zachary, LA (US); James D. Sunderhaus, Baton Rouge, LA (US); James J. Springer, Saugatuck, MI (US)

(73) Assignee: Albemarle Corporation, Baton Rouge, LA (US)

( * ) Notice: Subject to any disclaimer, the term of this patent is extended or adjusted under 35 U.S.C. 154(b) by 0 days.

(21) Appl. No.: 15/529,186

(22) PCT Filed: Oct. 5, 2015

(86) PCT No.: PCT/US2015/053993
§ 371 (c)(1),
(2) Date: May 24, 2017

(87) PCT Pub. No.: WO2016/105619
PCT Pub. Date: Jun. 30, 2016

(65) Prior Publication Data
US 2017/0334854 A1    Nov. 23, 2017

Related U.S. Application Data

(60) Provisional application No. 62/096,192, filed on Dec. 23, 2014.

(51) Int. Cl.
| C07D 213/50 | (2006.01) |
| C07D 403/06 | (2006.01) |
| B01J 23/44 | (2006.01) |
| B01J 31/24 | (2006.01) |

(52) U.S. Cl.
CPC ............ *C07D 213/50* (2013.01); *B01J 23/44* (2013.01); *B01J 31/2404* (2013.01); *C07D 403/06* (2013.01)

(58) Field of Classification Search
CPC .................................................. C07D 213/50
USPC ....................................................... 546/262
See application file for complete search history.

(56) References Cited

U.S. PATENT DOCUMENTS

| 3,118,898 A | 1/1964 | Yost |
| 6,057,456 A | 5/2000 | Hartwig et al. |
| 6,072,073 A | 6/2000 | Kawatsura et al. |
| 2017/0305948 A1* | 10/2017 | Hazari .................. C07F 17/02 |

FOREIGN PATENT DOCUMENTS

| CN | 102464610 A | 5/2012 |
| WO | 2007000435 A1 | 1/2007 |

OTHER PUBLICATIONS

Noeel, "Chloro(2-dicyclohexyl, etc.," e-EROS Encyclopedia of Reagents for Organic Synthesis, John Wiley, 1-5 (Year: 2011).*
Dorwald et al., Side reactions in Organic Synthesis, Wiley: VCH Weinheim Preface, pp. 1-15 and Chapter 8, pp. 279-308. (Year: 2005).*
Bencze, W.L. et al.; "Amphenone Analogs. III. Pinacol—Pinacolone Type Rearrangement in the Pyridine Series"; J. Am. Chem. Soc.; vol. 81, Aug. 5, 1959; pp. 4015-4018.
Bencze, W.L. et al.; "Photochemical Preparation, Rearrangement, and Dehydration of Symmetrical Methyl and Phenyl Pyridyl Glycols"; Journal of Organic Chemistry; vol. 27; Aug. 1962; pp. 2865-2870.
Biscoe, Mark R. et al.; "Selective Monoarylation of Acetate Esters and Aryl Methyl Ketones Using Aryl Chlorides"; Organic Letters; vol. 11, No. 8; 2009; pp. 1773-1775.
Kawatsura, Motoi et al.; "Simple, Highly Active Palladium Catalysts for Ketone and Malonate Arylation: Dissecting the Importance of Chelation and Steric Hindrance"; J. Am. Chem. Soc.; vol. 121; 1999; pp. 1473-1478.
Lee, Jin Ho et al.; "Palladium-Catalyzed α-Arylation of Aryloxyketones for the Synthesis of 2,3-Disubstituted Benzofurans"; The Journal of Organic Chemistry; vol. 79; 2014; pp. 6153-6163.
Linshoeft, Julian et al.; "Chemoselective Cross-Coupling Reactions with Differentiation Between Two Nucleophilic Sites on a Single Aromatic Substrate"; Organic Letters; vol. 14, No. 22; 2012; pp. 5644-5647.

* cited by examiner

*Primary Examiner* — Patricia L Morris
(74) *Attorney, Agent, or Firm* — Troy S. Kleckley

(57) ABSTRACT

Process for preparing metyrapone type compounds are generally described herein. In particular, one step process for preparing metyrapone type compounds are described herein. Such processes generally include an alpha-carbon arylation coupling reaction between 3-isobutyrylpyridine and 3-halopyridine compounds in the presence of a palladium catalyst and a phosphine ligand to form the metyrapone-type compounds.

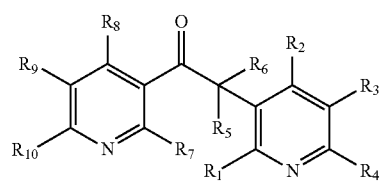

19 Claims, No Drawings

PROCESS FOR THE SYNTHESIS OF METYRAPONE AND ALKYLATED METYRAPONE ANALOGS

CROSS-REFERENCE TO RELATED APPLICATIONS

This application is a National Stage of International Application No. PCT/US2015/053993, filed on Oct. 5, 2015, which application claims priority from U.S. Application No. 62/096,192, filed Dec. 23, 2014. Each patent application identified above is incorporated here by reference in its entirety.

TECHNICAL FIELD

The invention disclosed pertains to a process for preparation of poly-heterocyclic compounds having quaternary alpha carbon atoms by a palladium catalyzed arylation of a ketone alpha carbon atom.

BACKGROUND

Methods known in the art for the synthesis of metyrapone generally include two-steps. The first step involves the preparation of a pinacol substrate generally formed from two equivalents of 3-acetylpyridine substrate. A symmetric compound, 2,3-dipyridine-3-yl-2,3-butanediol, is formed, in a reaction which involves the formation of two adjacent quaternary centers. In general, the formation of quaternary centers is made more difficult by the presence of large substituent groups at the potential quaternary carbon atoms. In the case of the reaction above, each potential quaternary carbon bears a pyridine substituent and a carbonyl oxygen in addition to a methyl group. Such substituents, particularly a group as bulky as pyridine, hinder the formation of the quaternary center. It is thus necessary to use another method in which the first step, which forms two such centers adjacent each other, is generally run at extreme or unusual conditions. An electrochemical step or a chemical step involving mercury or mercury salts is most commonly used.

The second step involves the rearrangement reaction of 2,3-dipyridine-3-yl-2,3-butanediol. As with the first step, the second step is fraught with problems which reduce the yield. In rearrangement reactions, a substituent shifts carbon centers. In the case of 2,3-dipyridine-3-yl-2,3-butanediol, one of two groups (pyridine, methyl) can undergo the shift. The desired product, metyrapone, is formed with significant amounts of a ketone byproduct, which reduces metyrapone yield and purity. Resolution of the resultant mixture is necessary. One method of resolution is the separation of the metyrapone and ketone byproduct by chromatographic methods. Another method involves derivatization as an oxime, followed by crystallization of the derivative, with a final hydrolysis step to give metyrapone. Both resolution methods contribute to a lowering of the yield of metyrapone.

The formation of 2,3-dipyridine-3-yl-2,3-butanediol, and the subsequent rearrangement reaction are illustrated below:

Current Literature Process

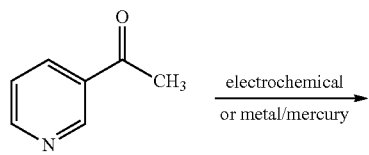

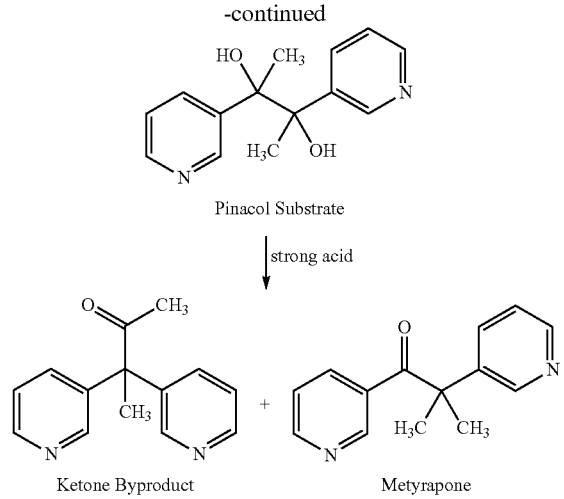

Literature publications in the late 1990's demonstrated that carbon-to-carbon bond connections could be made with palladium-catalyzed reactions using halogenated aromatic compounds. Various methods of preparing similar compounds have been tried. For example, a publication authored by Kawatsura and Hartwig (J. Am Chem. Soc., Vol. 121. No. 7, 1999), discloses the alpha arylation of ketones with aryl bromides with the use of palladium containing catalysts. The reference also discloses the formation of a quaternary carbon centers, albeit without the use of heterocyclic reactants.

However, the palladium catalyzed arylations of ketone alpha carbon atoms, particularly to form a quaternary center at the alpha carbon, are beset with unpredictability for at least two reasons. First, palladium catalysts are known to participate in the formation of ligand complexes with nitrogen containing heterocyclic aryl groups. Furthermore, some compounds containing multiple ligand-forming heterocycles such as pyridine are known to form particularly stable complexes with palladium-containing catalysts due to the "chelate effect." Metyrapone is part of this group in that metyrapone includes two pyridine groups. Such complexes are expected to interfere with or prevent the formation of necessary intermediate complexes involving the palladium catalyst and the reactant molecules. The chelate effect refers to the enhanced stability of chelate complexes (metal/ligand complexes derived from multidentate ligands), as opposed to complexes derived from one or more monodentate ligands. In its fully bonded state, the chelating ligand at least partially surrounds the central atom. The ligand need not have the same number of ligating groups as the number of bonding metal orbitals. For example, the notably stable dimethylglyoximate complex of nickel is a synthetic macrocycle derived from the anion of dimethylglyoxime. Nickel has four bonding sites and the ligand consists of two dimethylglyoxime molecules having two ligands each. The chelate structure is a central atom at the center of a ring structure. It is generally recognized that the chelate effect greatly stabilizes chelates with respect to mono-ligand containing complexes, and the enhanced stability favors the displacement of a number of monodentate ligands by a smaller number of polydentate ligands. In the case of using the reaction in the reference to form metyrapone, the indicated reaction would be the alpha arylation of 3-isobutyryl pyridine with a 3-halopyridine. One of skill in the art would recognize that the metyrapone product, a molecule having two pyridines, each of which are capable of bonding to one of the six palladium bonding orbitals, could be a suitable chelating ligand, according to common chemical knowledge. In such a case, the reaction would not be expected to proceed because the first molecules of product would form stable complexes with the catalyst, resisting displacement by reactant molecules, which are monodentate.

Yet a further factor which is expected to help the ability of the product to employ all of its pyridine groups is their relative placement. The length of the linking groups between the pyridine groups can be too short or too bulky to permit efficient coordination of all the pyridine groups.

The second reason the results of palladium-catalyzed arylations can be difficult to predict is that the use of palladium catalysts is subject to steric constraints that are not well-understood. The degree to which a palladium catalyst effects the arylation, if arylation even occurs at all, can depend critically upon the particular palladium catalyst, auxiliary ligands, the size of the alkanyl substituent to be arylated, as well as the base, and even the solvent. Thus, regardless of the possibility of product/catalyst interaction, the reaction may only produce an insignificant amount of product, if any at all. For example, the experiment of Example Ib essentially reproduces a run from (Biscoe & Buchwald, *Organic Letters*, 11, 1773 (2009)), except for the use of 3-isobutyrylpyridine as a reactant (in an attempt to form metyrapone) rather than 3-acetylpyridine as used in the reference. No product was observed, despite the fact that the reference reaction did form product. With the substitution, the reaction does not proceed at all, even with the same catalyst and under the same conditions as used in the reference. Furthermore, the lack of product tends to indicate that the lack of reaction was not due to catalyst chelation, but rather the difficulty in forming the quaternary center necessary for the formation of metyrapone. Thus, reaction success can depend upon steric characteristics of the two reactants.

Metyrapone, a commercial product of high value long before the publication of the coupling methods described above, is presently prepared through the two-step process described above, despite relatively low yields and high amounts of byproduct impurities. A process which can prepare poly-heterocyclic compounds, such as metyrapone, by arylating the alpha carbon atom of a ketone, to form a quaternary center thereat, would be an advance in the art.

BRIEF SUMMARY

We have discovered that metyrapone, 2-methyl-1,2-di-3-pyridyl-1-propanone, can be prepared in one step by the palladium catalyzed coupling of the enolate of 3-isobutyrylpyridine with 3-bromopyridine. The yield of this step is high, and isomeric byproducts are avoided. The reaction can be summarized as follows:

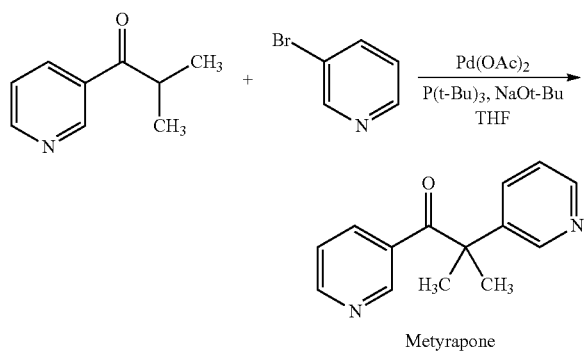

Metyrapone

In general, it has been found that an alpha-carbon arylation coupling reaction can be effected between 3-isobutyrylpyridine and 3-halopyridine compounds in the presence of a palladium catalyst and a phosphine ligand to make metyrapone-type compounds.

Accordingly, provided is a process for the preparation of a product compound of the following general formula:

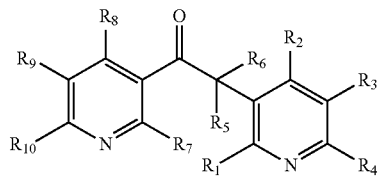

said process comprising:
1) forming a reaction mixture comprising
   i) a halopyridine of the following structure:

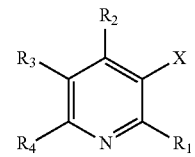

ii) a substituted pyridine of the following structure:

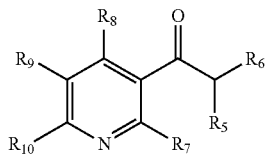

iii) a palladium containing catalyst selected from the group consisting of palladium(II) acetate, bis(dibenzylideneacetone)palladium(0), tris(dibenzylideneacetone)dipalladium(0), tetrakis(triphenylphosphine)palladium(0), and [1,1'-bis(diphenylphosphino)ferrocene]dichloropalladium(II);
   iv) a phosphine or carbine ligand;
   v) a Bronsted base; and
   vi) a solvent;
   and
2) heating the reaction mixture to one or more temperatures in the range of about 30 to about 110° C. such that the product compound is formed;
wherein $R_1$, $R_2$, $R_3$, $R_4$, $R_7$, $R_8$, $R_9$ and $R_{10}$ are each, independently, hydrogen or an alkyl group comprising in the range of one to four carbon atoms; $R_5$ and $R_6$ are each, independently, an alkyl group comprising in the range of from one to three carbon atoms, and X is selected from the group consisting of chlorine, bromine and iodine. In other aspects, X is sulfonate, triflate, nonaflate or a diazonium salt.

This and other aspects and features of the invention will become even more apparent from the following detailed description of the invention and the appended aspects.

DETAILED DESCRIPTION

The halopyridine reactant can be a chloro-, a bromo- or an iodopyridine, with a bromo- or iodopyridine preferred, and a bromopyridine most preferred. In other aspects, X is sulfonate, triflate, nonaflate or a diazonium salt. In some aspects of the invention, the sulfonate ester of 3-hydroxypyridine can be used. In some aspects of the invention, $R_1$, $R_2$, $R_3$ and $R_4$ are each, independently, hydrogen, or an alkyl groups comprising in the range of one to four carbon atoms. In other aspects, the halopyridine is a chloropyridine, and in still further aspects the halopyridine is an unsubstituted halopyridine.

The substituted pyridine used in the process comprises a tertiary alpha carbon atom such that, upon arylation, a quaternary center is established at the alpha carbon. In one aspect of the invention $R_5$ and $R_6$ are each, independently, an alkyl groups having in the range of one to five, or in other aspects, one to three carbon atoms. In yet another aspect, $R_5$ and $R_6$ are each methyl. In one aspect of the invention, $R_7$, $R_8$, $R_9$ and $R_{10}$ are, each independently, hydrogen, or an alkyl groups comprising in the range of one to four carbon atoms. In yet another aspect, $R_7$, $R_8$, $R_9$ and $R_{10}$ are each hydrogen, and in a further aspect, additionally, $R_5$ and $R_6$ are each methyl groups. In a preferred aspect, the halopyridine is a bromopyridine; $R_1$, $R_2$, $R_3$ and $R_4$ of the halopyridine and $R_7$, $R_8$, $R_9$ and $R_{10}$ of the substituted pyridine are each hydrogen; and $R_5$ and $R_6$ are each methyl groups.

The structures for the halopyridine and the substituted pyridine depict the halogen and the acyl substituent, respectively, in the meta position with respect to the nitrogen. However, it is thought that an ortho or para relationship, particularly concerning the halopyridine, could give a viable reaction.

The phosphine ligand is selected from among one or more of the following groups:
a) Trialkyl/aryl phosphines comprising substituents independently selected from tert-butyl-, cyclohexyl-, adamantyl-, or other bulky substituents. By trialkyl/aryl, it is meant that the three ligands consist of any combination of alkyl and aryl groups. Also included in the trialkyl/aryl class are Buchwald-type ligands or pre-catalysts such as dialkylbiaryl monophosphenes such as, for example, dicyclohexylphosphino-2',4',6'-triisopropylbiphenyl (Xphos™). Other Buchwald-types include 2-di-tert-butylphosphino-2',4',6'-triisopropylbiphenyl (tBuXPhos™); (2-biphenyl)di-tert-butylphosphine (JohnPhos™); (2-biphenyl) dicyclohexylphosphine (CyJohnPhos™); 2-dicyclohexylphosphino-2',6'-dimethoxybiphenyl (Sphos™); 2-dicyclohexylphosphino-2',6'-diisopropoxybiphenyl (RuPhos)™; 2-dicyclohexylphosphino-2'-(N,N-dimethylamino) biphenyl (DavePhos™); 2-di-tert-butylphosphino-2'-methylbiphenyl (tBuMePhos™); 2-dicyclohexylphosphino-2'-methylbiphenyl (MePhos™); Preferred are tri-tert-butylphosphine and tricyclohexylphosphine;
b) Phosphine ligands selected from selected from the following group: 4,5-bis(diphenylphosphino)-9,9-dimethylxanthene (Xantphos™), 9,9-dimethyl-4,5-bis(di-tert-butylphosphino)xanthene (t-Bu-Xantphos™), 2,2'-bis(diphenylphosphino)-1,1'-binaphthalene (BINAP), and 1,1'-bis(diphenylphosphino)ferrocene (dppf), 1,2,3,4,5-pentaphenyl-1'-(di-tert-butylphosphino)ferrocene (QPhos™);
c) an N-heterocyclic carbene containing ligand or catalyst selected from the group consisting of: such as, for example, 1,3-bis(2,6-diisopropylphenyl)-4,5-dihydroimidazolium tetrafluoroborate (SIPr—HBF$_4$); 1,3-bis-(2,6-diisopropylphenyl) imidazolinium chloride; 1,3-dimesitylimidazolidinium chloride, 4,5-dihydro-1,3-bis(2,4,6-trimethylphenyl)-1H-imidazolium chloride; 1,3-bis(tricyclo[3.3.1.1$^{3,7}$]dec-1-yl)- 1H-imidazolium tetrafluoroborate; 1,3-bis(2,4,6-trimethylphenyl)imidazolinium chloride; (1,3-bis(2,6-diisopropylphenyl)imidazolidene) (3-chloropyridyl) palladium(II) dichloride; (PEPPSI™-SIPr catalyst); [1,3-bis (2,6-Diisopropylphenyl)imidazol-2-ylidene](3-chloropyridyl)palladium(II); and dichloride (PEPPSI™-IPr catalyst).

It should be noted that some of the N-heterocyclic carbine ligands also contain palladium and are thus catalyst/ligand complexes as added. The foregoing can be the case for the Buchwald ligands as well. In such cases the palladium catalyst is already present, and a separate palladium catalyst, below, is not strictly necessary.

The palladium catalyst is selected from the group consisting of palladium(II) acetate, bis(dibenzylideneacetone) palladium(0), tris(dibenzylideneacetone)dipalladium(0), tetrakis(triphenylphosphine)palladium(0), and [1,1'-bis(diphenylphosphino)ferrocene] dichloropalladium(II). In a preferred aspect, the catalyst is palladium(II) acetate. In other aspects, the catalyst can be a mixture of two or more of the above.

The base is selected from lithium t-butoxide, sodium t-butoxide, potassium t-butoxide, lithium bis(trimethylsilyl) amide, sodium bis(trimethylsilyl)amide, potassium bis(trimethylsilyl)amide, lithium diisopropylamide, lithium dicyclohexylamide, cesium carbonate, and potassium phosphate. Hydrides, such as sodium hydride and potassium hydride, and carbonates, such as, for example sodium carbonate, can be used as well. In a preferred aspect, the base is sodium t-butoxide. In other aspects, the base can be a mixture of two or more of the above.

The solvent is selected from tetrahydrofuran; 2-methyltetrahydrofuran; 1,4-dioxane, dimethoxyethane; and toluene. In a preferred aspect, the solvent is tetrahydrofuran. In other aspects, the solvent can be a mixture of two or more of the above.

The reactants and solvent can be combined in any order to make the reaction mixture. It can be convenient to combine the palladium catalyst, phosphine ligand and base to form a dry mixture in a reaction vessel, adding the halopyridine, the substituted pyridine and the solvent on top of the dry mixture.

The reaction generally will proceed to substantial completion if heated at appropriate temperatures for sufficient times. Thus, stoichiometric equivalents of the halopyridine and the substituted pyridine can be used. The palladium catalyst and phosphine ligand are preferably used in a molar ratio in the range of from about 1 to about 5 moles of ligand per mole of palladium catalyst, with a ratio in the range of about 1 to about 2 moles of ligand per mole of palladium catalyst preferred. In general the ligand and catalyst each comprise from about 0.05 to about 10 mol % based upon moles of substrate, with about 0.1 to about 5 mol % preferred. The amount of solvent used should be sufficient to solvate the dry ingredients, and other than that concern, the amount used is not deemed to be critical. In general, the payload (i.e., the amount of both reactants combined relative to the amount of solvent) is most conveniently in the range of about 1 to about 30 wt %.

The reaction mixture is then heated. It can be convenient to heat to the reflux temperature of the solvent for the duration of the reaction. In general, the reaction mixture is heated to one or more temperatures in the range of about 30 to about 110° C., for time in the range of about 0.5 to about 24 hours. In one aspect of the invention, the reaction mixture is heated to one or more temperatures in the range of about 45 to about 100° C. In another aspect of the invention, the heating time is in the range of about 1 to about 6 hours. In yet another aspect, the heating time is in the range of about 2 to about 4 hours. In a preferred aspect, the reaction mixture is heated to one or more temperatures in the range of about 80 to about 110° C. for a time in the range of about 2 to about 4 hours.

After the reaction has reached completion, it can be quenched, such as with ammonium chloride, water or other reagent which removes or inactivates the base, preferably after cooling the reaction somewhat, such as to room temperature.

The product can be separated using extraction, such as with ethyl acetate. In general, yield can be in the range of from about 70% to about 90% based upon the weight of the halopyridine. Purity can be in the range of about 90% to greater than 99% GC area % after purification.

Example Ib, below, is a counterexample which reproduces a run from Biscoe & Buchwald, *Organic Letters,* 11, 1773 (2009), except for the use of 3-isobutyrylpyridine as a reactant, which would be expected to form metyrapone, rather than 3-acetylpyridine as used in the reference. Despite the fact that the reference reaction did form product, no product was observed. With the substitution, the reaction does not proceed at all, even with the same catalyst and under the same conditions as used in the reference. Thus, even in the absence of chelation, the difficulty in forming the quaternary center necessary for the formation of metyrapone can prevent the formation of product.

Example Ia

Preparation of Metyrapone with a Pd(OAc)$_2$ Catalyst

Pd(OAc)$_2$ (15 mg, 0.067 mmol); P(-t-Bu)$_3$ (15 mg, 0.074 mmol); and NaO-t-Bu (199 mg, 2.07 mmol) were weighed into a round bottom flask in a nitrogen purge box. The flask was removed from the purge box and THF (10 mL), 3-bromopyridine (0.17 mL, 279 mg, 1.76 mmol) and 3-isobutyrylpyridine (251 mg, 1.68 mmol) were added. The reaction was heated under reflux for 3.5 h. The reaction was cooled to room temperature and quenched with saturated aqueous NH$_4$Cl (10 mL). The mixture was extracted with EtOAc (2×10 mL). The organic phases were combined and washed with saturated aqueous NaCl (10 mL), dried (MgSO$_4$), filtered, and concentrated under reduced to give the crude metyrapone that was 80% pure by GC-MS.

Example Ib

XPhos precatalyst (32 mg, 0.043 mmol) and KOt-Bu (348 mg, 3.10 mmol) were weighed into a round bottom flask in a nitrogen purge box. The flask was removed from the purge box and 3-chloropyridine (0.17 mL, 202 mg, 1.79 mmol), 3-isobutyrylpyridine (255 mg, 1.71 mmol) and toluene (7 mL), were added. The reaction was heated to 60° C. for 3 h. A 0.15 mL aliquot was removed and the reaction progressed checked by GC-MS. GC-MS showed only unreacted starting material. The reaction was heated to 80° C. and maintained there for 3 hours, and then heated to 90° C. maintained there for 16 hours. The reaction was cooled to room temperature and quenched with saturated aqueous NH$_4$Cl (10 mL). The mixture was extracted with EtOAc (2×10 mL). The organic phases were combined and washed with saturated aqueous NaCl (10 mL), dried (MgSO$_4$), filtered, and concentrated. Analysis of the crude reaction mixture (365 mg) by GC-MS showed that no metyrapone was produced during the reaction and that the mixture was predominately recovered starting material.

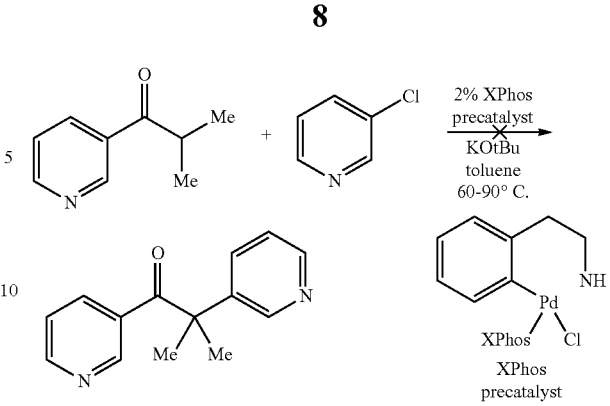

Components referred to by chemical name or formula anywhere in the specification or aspects hereof, whether referred to in the singular or plural, are identified as they exist prior to coming into contact with another substance referred to by chemical name or chemical type (e.g., another component, a solvent, or etc.). It matters not what chemical changes, transformations and/or reactions, if any, take place in the resulting mixture or solution as such changes, transformations, and/or reactions are the natural result of bringing the specified components together under the conditions called for pursuant to this disclosure. Thus the components are identified as ingredients to be brought together in connection with performing a desired operation or in forming a desired composition. Also, even though the aspects hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. The fact that a substance, component or ingredient may have lost its original identity through a chemical reaction or transformation during the course of contacting, blending or mixing operations, if conducted in accordance with this disclosure and with ordinary skill of a chemist, is thus of no practical concern.

The invention may comprise, consist, or consist essentially of the materials and/or procedures recited herein.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about", the aspects include equivalents to the quantities.

Except as may be expressly otherwise indicated, the article "a" or "an" if and as used herein is not intended to limit, and should not be construed as limiting, the description or an aspect to a single element to which the article refers. Rather, the article "a" or "an" if and as used herein is intended to cover one or more such elements, unless the text expressly indicates otherwise.

Each and every patent or other publication or published document referred to in any portion of this specification is incorporated in tow into this disclosure by reference, as if fully set forth herein.

This invention is susceptible to considerable variation in its practice. Therefore the foregoing description is not intended to limit, and should not be construed as limiting, the invention to the particular exemplifications presented hereinabove.

The invention claimed is:
1. A process for the preparation of a compound having the following formula:

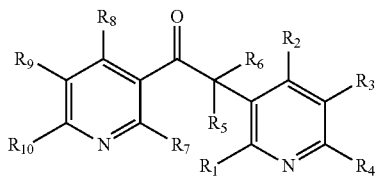

the process comprising the steps of:
1) preparing a reaction mixture from at least:
   i) a halopyridine of the following structure:

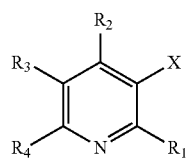

ii) a substituted pyridine of the following structure:

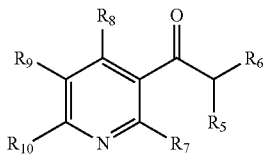

iii) a palladium containing catalyst, if iv) does not comprise palladium;
   iv) a phosphine or carbene ligand;
   v) a Bronsted base; and
   vi) a solvent;
2) heating the reaction mixture to one or more temperatures in the range of about 30° C. to about 110° C. such that the compound is formed;
wherein $R_1$, $R_2$, $R_3$, and $R_4$, are each, independently, hydrogen or an alkyl group comprising in the range of one to four carbon atoms, $R_5$ and $R_6$ are each methyl groups, $R_7$, $R_8$, $R_9$ and $R_{10}$ are each hydrogen, and X is selected from the group consisting of chlorine, bromine, iodine, sulfonate, triflate, nonaflate, and a diazonium salt.

2. The process of claim 1, wherein the phosphine ligand is selected from the group consisting of:
a) a trialkyl/aryl phosphine comprising substituents independently selected from the group consisting of tert-butyl-, cyclohexyl, and adamantyl-;
b) a trialkyl/aryl phosphine selected from the group consisting of dicyclohexylphosphino-2',4',6'-triisopropylbiphenyl (Xphos™), 2-di-tert-butylphosphino-2',4', 6'-triisopropylbiphenyl (tBuXPhos™); (2-biphenyl)di-tert-butylphosphine (JohnPhos™); (2-biphenyl) dicyclohexylphosphine (CyJohnPhos™); 2-dicyclohexylphosphino-2',6'-dimethoxybiphenyl (Sphos™); 2-dicyclohexylphosphino-2',6'-diisopropoxybiphenyl (RuPhos™); 2-dicyclohexylphosphino-2'-(N,N-dimethylamino) biphenyl (DavePhos™); 2-di-tert-butylphosphino-2'-methylbiphenyl (tBuMePhos™); 2-dicyclohexylphosphino-2'-methylbiphenyl (MePhos™), tri tert-butylphosphine and tricyclohexylphosphine; and
c) a phosphine ligand selected from the group consisting of 4,5-bis(diphenylphosphino)-9,9-dimethylxanthene (Xantphos), 9,9-Dimethyl-4,5-bis(di-tert-butylphosphino)xanthene (t-Bu-Xantphos), 2,2'-bis(diphenylphosphino)-1,1'-binaphthalene (BINAP), and 1,1'-Bis (diphenylphosphino)ferrocene (dppf), 1,2,3,4,5-Pentaphenyl-1'-(di-tert-butylphosphino)ferrocene (QPhos).

3. The process of claim 1, wherein the palladium catalyst is selected from the group consisting of palladium(II) acetate, bis(dibenzylideneacetone)palladium(0), tris(dibenzylideneacetone)dipalladium(0), tetrakis(triphenylphosphine)palladium(0), [1,1'-bis(diphenylphosphino)ferrocene] dichloropalladium(II), and any mixture thereof.

4. The process of claim 1 wherein the Bronsted base is selected from the group consisting of lithium t-butoxide, sodium t-butoxide, potassium t-butoxide, lithium bis(trimethylsilyl)amide, sodium bis(trimethylsilyl)amide, potassium bis(trimethylsilyl)amide, lithium diisopropylamide, lithium dicyclohexylamide, cesium carbonate, potassium phosphate, and any mixture thereof.

5. The process of claim 1, wherein the solvent is selected from the group consisting of tetrahydrofuran, 2-methyltetrahydrofuran, 1,4-dioxane, dimethoxyethane, toluene; and any mixture thereof.

6. The process of claim 1, wherein the carbene ligand is selected from the group consisting of 1,3-bis(2,6-diisopropylphenyl)-4,5-dihydroimidazolium tetrafluoroborate (SIPr—HBF$_4$); 1,3-bis-(2,6-diisopropylphenyl)imidazolinium chloride; 1,3-dimesitylimidazolidinium chloride, 4,5-dihydro-1,3-bis(2,4,6-trimethylphenyl)-1H-imidazolium chloride; 1,3-bis(tricyclo[3.3.1.1$^{3,7}$]dec-1-yl)-1H-imidazolium tetrafluoroborate; 1,3-bis(2,4,6-trimethylphenyl)imidazolinium chloride; (1,3-bis(2,6-diisopropylphenyl)imidazolidene) (3-chloropyridyl) palladium(II) dichloride; (PEPPSI™-SIPr catalyst); [1,3-bis(2,6-Diisopropylphenyl) imidazol-2-ylidene](3-chloropyridyl)palladium(II); and dichloride (PEPPSI™-IPr catalyst).

7. The process of claim 1 wherein $R_1$, $R_2$, $R_3$ and $R_4$ are each hydrogen.

8. The process of claim 1 wherein the substituted pyridine is 3-isobutyrylpyridine.

9. The process of claim 8 wherein the halopyridine is selected from the group consisting of chloropyridine, bromopyridine, and iodopyridine.

10. The process of claim 9 wherein the palladium containing catalyst is selected from the group consisting of (dibenzylideneacetone)palladium(0), tris(dibenzylideneacetone)dipalladium(0), tetrakis(triphenylphosphine)palladium(0), [1,1'-bis(diphenylphosphino)ferrocene]dichloropalladium(II), and any mixture thereof.

11. The process of claim 10 wherein the solvent is tetrahydrofuran, toluene, or any mixture thereof.

12. The process of claim 1 wherein the palladium containing catalyst and phosphine ligand have a molar ratio in the range of from 1 to 5 moles of ligand per mole of palladium containing catalyst.

13. The process of claim 1 wherein the heating of the reaction mixture in 2) is to one or more temperatures in the range of about 80° C. to about 110° C. for a time in the range of 2 hours to 4 hours.

14. The process of claim 1 further comprising quenching the reaction mixture with a reagent that removes or inactivates the Bronsted base.

15. A process for the preparation of a compound having the following formula:

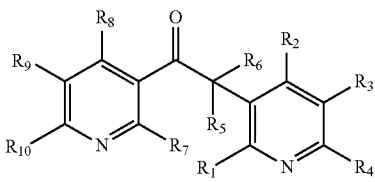

the process comprising the steps of:
1) preparing a reaction mixture from at least:
   i) a halopyridine selected from the group consisting of chloropyridine, bromopyridine, and iodopyridine;
   ii) 3-isobutyrylpyridine
   iii) a palladium containing catalyst;
   iv) a phosphine or carbene ligand;
   v) a Bronsted base; and
   vi) a solvent;
2) heating the reaction mixture to one or more temperatures in the range of about 30° C. to about 110° C. such that the compound is formed;
wherein $R_1$, $R_2$, $R_3$, $R_4$, $R_7$, $R_8$, $R_9$ and $R_{10}$ are each hydrogen, $R_5$ and $R_6$ are each methyl groups, and X is selected from the group consisting of chlorine, bromine, iodine, sulfonate, triflate, nonaflate and a diazonium salt.

16. The process of claim 15, wherein the phosphine ligand is selected from the group consisting of:
a) a trialkyl/aryl phosphine comprising substituents independently selected from the group consisting of tert-butyl-, cyclohexyl, and adamantyl-;
b) a trialkyl/aryl phosphine selected from the group consisting of dicyclohexylphosphino-2',4',6'-triisopropylbiphenyl (Xphos™), 2-di-tert-butylphosphino-2',4',6'-triisopropylbiphenyl (tBuXPhos™); (2-biphenyl)di-tert-butylphosphine (JohnPhos™); (2-biphenyl)dicyclohexylphosphine (CyJohnPhos™); 2-dicyclohexylphosphino-2',6'-dimethoxybiphenyl (Sphos™); 2-dicyclohexylphosphino-2',6'-diisopropoxybiphenyl (RuPhos™); 2-dicyclohexylphosphino-2'-(N,N-dimethylamino)biphenyl (DavePhos™); 2-di-tert-butylphosphino-2'-methylbiphenyl (tBuMePhos™); 2-dicyclohexylphosphino-2'-methylbiphenyl (MePhos™), tri-tert-butylphosphine and tricyclohexylphosphine; and
c) a phosphine ligand selected from the group consisting of 4,5-bis(diphenylphosphino)-9,9-dimethylxanthene (Xantphos), 9,9-Dimethyl-4,5-bis(di-tert-butylphosphino)xanthene (t-Bu-Xantphos), 2,2'-bis(diphenylphosphino)-1,1'-binaphthalene (BINAP), and 1,1'-Bis(diphenylphosphino)ferrocene (dppf), 1,2,3,4,5-Pentaphenyl-1'-(di-tert-butylphosphino)ferrocene (QPhos).

17. The process of claim 15 wherein the Bronsted base is selected from the group consisting of lithium t-butoxide, sodium t-butoxide, potassium t-butoxide, lithium bis(trimethylsilyl)amide, sodium bis(trimethylsilyl)amide, potassium bis(trimethylsilyl)amide, lithium diisopropylamide, lithium dicyclohexylamide, cesium carbonate, potassium phosphate, and any mixture thereof.

18. The process of claim 15, wherein the carbene ligand is selected from the group consisting of 1,3-bis(2,6-diisopropylphenyl)-4,5-dihydroimidazolium tetrafluoroborate (SIPr—HBF$_4$); 1,3-bis-(2,6-diisopropylphenyl)imidazolinium chloride; 1,3-dimesitylimidazolidinium chloride, 4,5-dihydro-1,3-bis(2,4,6-trimethylphenyl)-1H-imidazolium chloride; 1,3-bis(tricyclo[3.3.1.1$^{3,7}$]dec-1-yl)-1H-imidazolium tetrafluoroborate; 1,3-bis(2,4,6-trimethylphenyl)imidazolinium chloride; (1,3-bis(2,6-diisopropylphenyl)imidazolidene) (3-chloropyridyl) palladium(II) dichloride; (PEPPSI™-SIPr catalyst); [1,3-bis(2,6-Diisopropylphenyl) imidazol-2-ylidene](3-chloropyridyl)palladium(II); and dichloride (PEPPSI™-IPr catalyst).

19. The process of claim 15 wherein the palladium containing catalyst is selected from the group consisting of (dibenzylideneacetone)palladium(0), tris(dibenzylideneacetone)dipalladium(0), tetrakis(triphenylphosphine)palladium(0), [1,1'-bis(diphenylphosphino)ferrocene]dichloropalladium(II), and any mixture thereof.

* * * * *